United States Patent [19]

Wang

[11] Patent Number: 5,556,192

[45] Date of Patent: Sep. 17, 1996

[54] PERFUMER STRUCTURE WITH AN OPTICALLY CONTROLLED NIGHT LAMP

[75] Inventor: Shih-Lin Wang, Shin Tien, Taiwan

[73] Assignee: Yeti Shine Co., Ltd., Shin Tien, Taiwan

[21] Appl. No.: 504,053

[22] Filed: Jul. 18, 1995

[51] Int. Cl.[6] ............................................. F21V 23/00
[52] U.S. Cl. ..................... 362/276; 362/226; 362/253; 362/802; 392/390; 428/905; 439/929
[58] Field of Search .............................. 362/101, 96, 226, 362/253, 276, 802, 806; 219/217, 218, 229, 258; 239/60; 392/390, 391, 392, 386, 403, 405; 428/905; 439/577, 929

[56] References Cited

U.S. PATENT DOCUMENTS

| | | | |
|---|---|---|---|
| 2,931,880 | 4/1960 | Yaffe | 392/390 |
| 3,968,355 | 7/1976 | Smallegan | 362/226 |
| 4,084,079 | 4/1978 | Costello | 392/390 |
| 4,549,250 | 10/1985 | Spector | 362/226 |
| 4,849,606 | 7/1989 | Martens, III et al. | 392/390 |
| 5,136,684 | 8/1992 | Lonker et al. | 392/390 |
| 5,213,523 | 5/1993 | Hygema et al. | 392/390 |
| 5,392,379 | 2/1995 | Fussell | 392/390 |

*Primary Examiner*—Denise L. Gromada
*Assistant Examiner*—Alan B. Cariaso
*Attorney, Agent, or Firm*—Jason Z. Lin

[57] ABSTRACT

A perfumer structure with an optically controlled night lamp is disclosed. The perfumer structure includes a heat conductor wrapped by a heat conductive and fireproof plastic material for generating heat to vaporize a solid perfume and uniformly disperse perfume gas. The night lamp is disposed in the perfumer structure and controlled by an optically sensitive element which turns on/off the lamp according to the ambient illumination. The perfumer structure is powered on via a single power plug and has both the functions of dispersing perfume gas to clean the air and illuminating at night.

1 Claim, 6 Drawing Sheets

PERFUMER STRUCTURE WITH AN OPTICALLY CONTROLLED NIGHT LAMP

BACKGROUND OF THE INVENTION

The present invention relates to a perfumer structure with an optically controlled night lamp. The perfumer structure is powered on via a single power plug and has both the functions of dispersing perfume gas to clean the air and illuminating at night.

A conventional perfumer is powered on via a power plug to generate heat for vaporizing a solid perfume into perfume gas. Such perfumer is generally provided with an indicator lamp which is turned on once the power plug is plugged into a power socket. The indicator lamp serves to indicate the power on state of the perfumer as well as show the position of the perfumer at night. Such indicator lamp will be continuously turned on by day and at night unless the plug is withdrawn from the socket. This causes waste of energy.

SUMMARY OF THE INVENTION

It is a primary object of the present invention to provide a perfumer structure with an optically controlled night lamp. The perfumer structure includes a heat conductor wrapped by a heat conductive and fireproof plastic material for generating heat to vaporize a solid perfume and uniformly disperse perfume gas for cleaning the air. The night lamp is disposed in the perfumer structure and controlled by an optically sensitive element which turns on/off the lamp according to the ambient illumination. The perfumer structure is powered on via a single power plug and has both the functions of dispersing perfume gas to clean the air and illuminating at night.

It is a further object of the present invention to provide the above perfumer structure in which no matter whether the night lamp is turned on/off, the perfumer always disperses perfume gas to clean the air.

It is still a further object of the present invention to provide the above perfumer structure in which the copper plates of the plug have two patterns to meet different specifications of power sockets in US or Taiwan. In addition, the heat conductor is integrally wrapped by and hidden in the heat conductive and fireproof plastic material so that the safety in use is ensured.

The features of the present invention in structure and function can be best understood through the following description and accompanying drawings, wherein:

DETAILED DESCRIPTION OF THE PREFERRED EMBODIMENTS

Figure 1B:
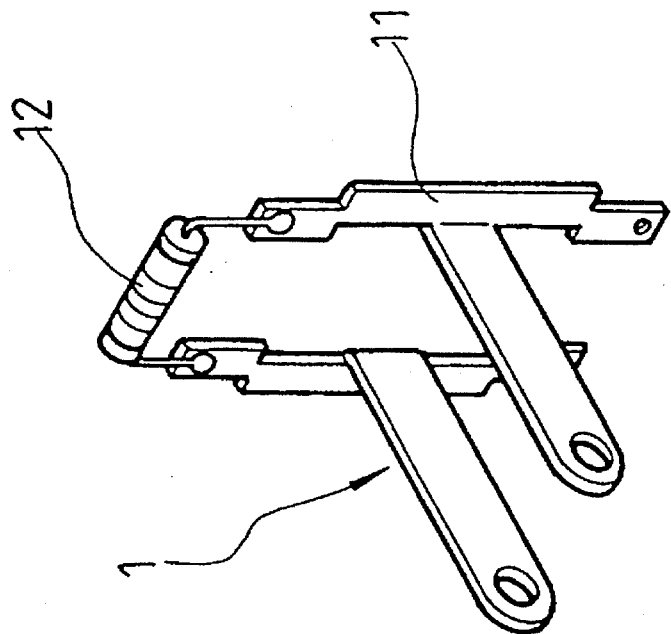
FIG. 1B is a perspective view of the bare copper plates and the heat conductor, in which the copper plates are arranged in another pattern.
Figure 1A:
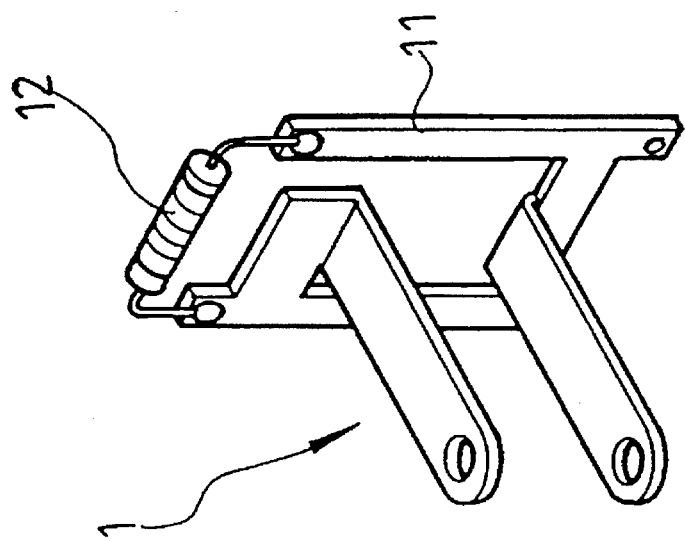
FIG. 1A is a perspective view of the bare copper plates of the plug and the heat conductor of the present invention.

Please refer to FIG. 1A. The plug 1 of the present invention includes two identical bare copper plates 11 which are arranged in reverse to each other to form a horizontally parallel pattern. A heat conductor 12 is welded between the copper plates 11 to form a circuit, whereby the current can pass through the heat conductor 12 to heat up the same. FIG. 1B shows another aspect of the plug 1 in which the copper plates are arranged in a vertically parallel pattern to suit different power socket.

Figure 2:
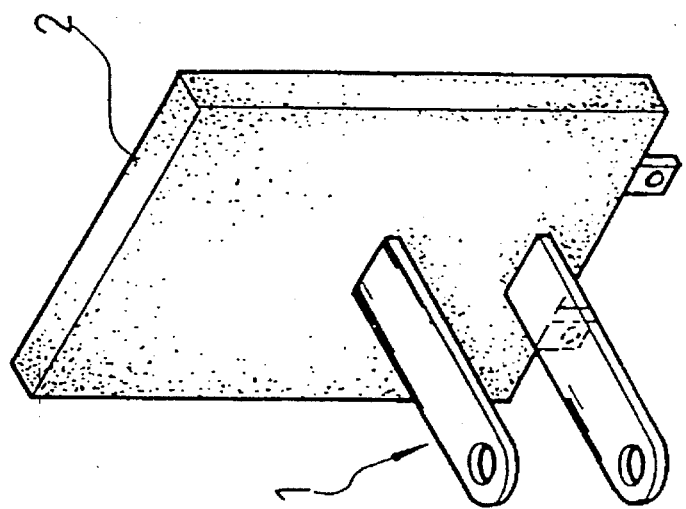
FIG. 2 is a perspective view showing that the copper plates and heat conductor are wrapped by a heat conductive and fireproof plastic material.

Referring to FIG. 2, the bare copper plates of FIG. 1A or 1B can be wrapped by a plastic material 2 which is heat conductive and fireproof. Accordingly, the heat conductor 12 is hidden in the plastic material 2 so as to protect a user from touching the copper plates 11 and being shocked. Moreover, by means of the plastic material 2, the heat conductor 12 can uniformly transmit the heat.

Figure 3:
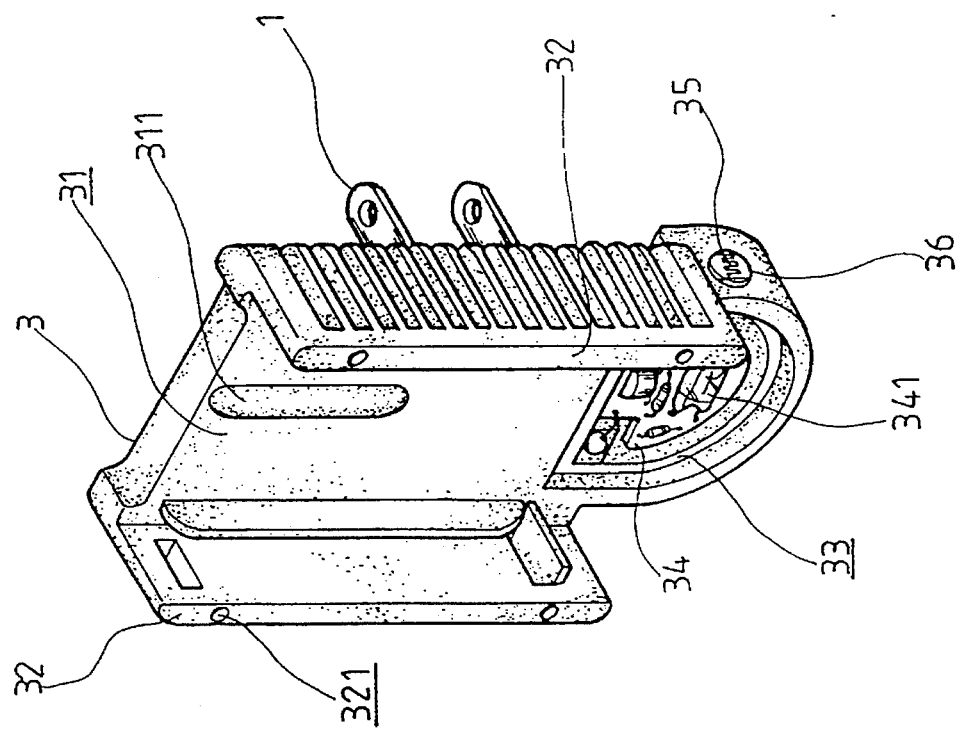
FIG. 3 is a perspective view of a housing of the present perfumer structure, which is integrally molded and associated with the plastic material of FIG. 2.
Figure 7:
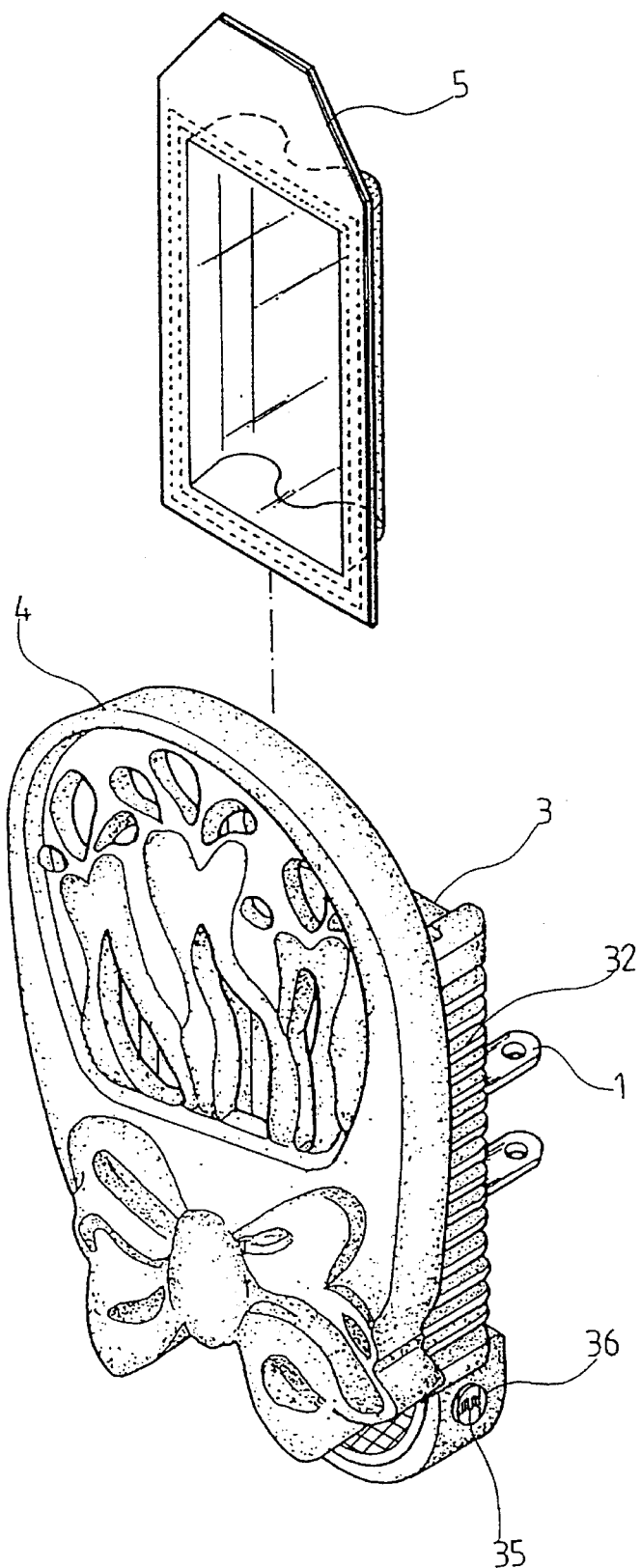
FIG. 7 shows the application of the present invention.

Referring to FIG. 3, the plastic material 2 of FIG. 2 is integrally associated with a housing 3 by injection molding. The housing 3 is formed with a central insertion channel 31 for locating a solid perfume 5 (as shown in FIG. 7) therein. Two lateral boards 32 are disposed on two sides of the insertion channel 31. Two locating holes 321 are formed on each lateral board 32. A convex guide rail 311 is disposed at a central portion of the insertion channel 31 for guiding the solid perfume 5 when inserted. The housing 3 has an arch receptacle 33 on a bottom thereof for receiving an optically controlled night lamp circuit board 34. The ends of the copper plates 11 are exposed in the receptacle 33 for electrically connecting with the circuit board 34. In the circuit board 34, a silicon controlled rectifier (SCR) converts AC into DC so as to supply power for a lamp 341. An optically sensitive element 35 is disposed on one side of the receptacle 33 for controlling the power supply for the lamp 341. An optically sensitive surface of the element 35 is exposed to ambient environment for receiving external light. A transparent cover 36 is overlaid on the element 35 for protecting the same. In the case that the external light is sufficient, the element 35 will not input any signal to the rectifier and thus the lamp 341 will not be powered on. While in the case that the external light is insufficient at night or in a dim place, the element 35 will activate the rectifier to turn on the lamp 341.

Figure 4:
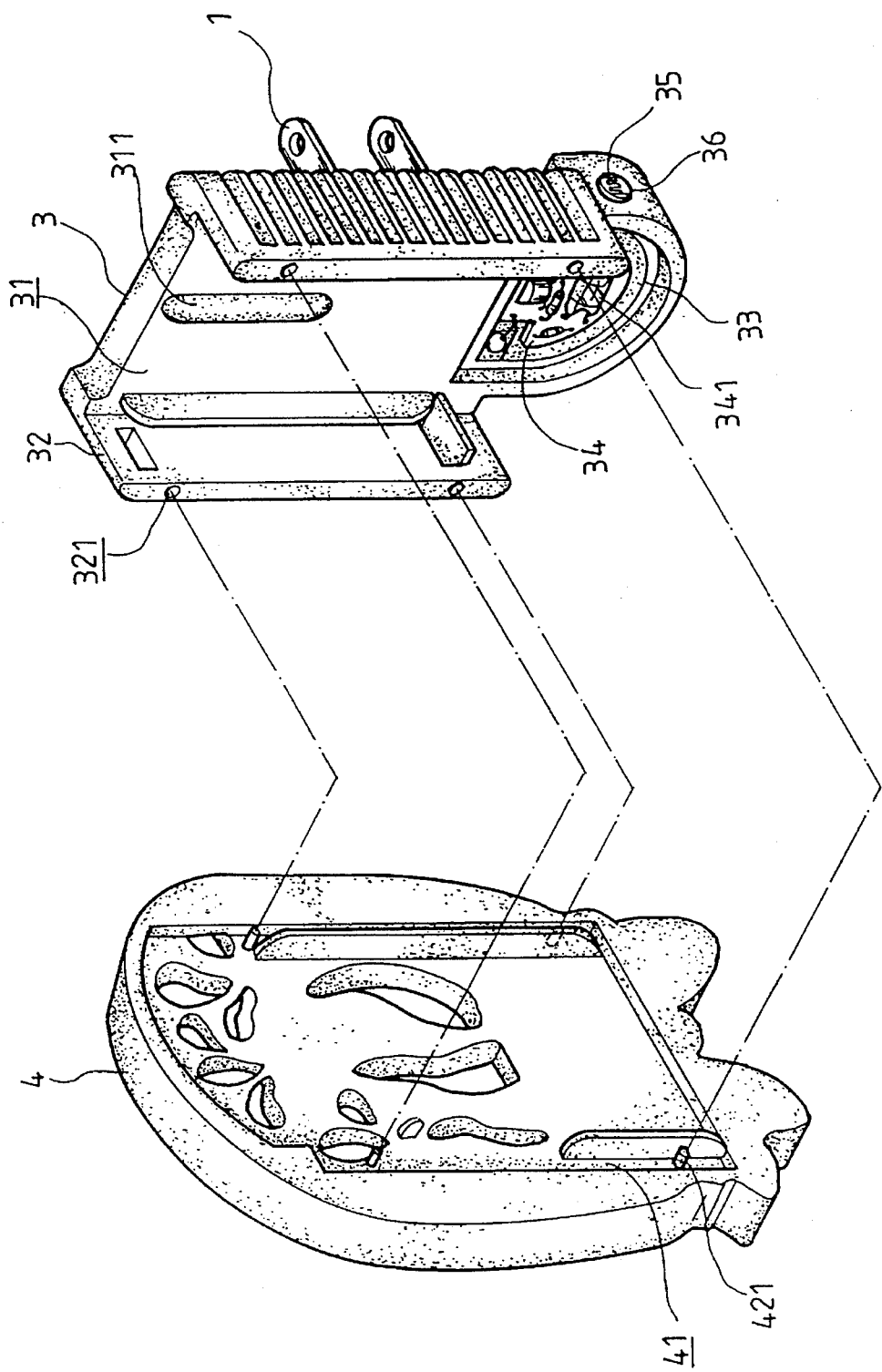
FIG. 4 is a perspective exploded view of the housing and face board of the present invention.

Referring to FIG. 4, a face board 4 can be associated with the housing 3. A front face of the face board 4 can be designed with various patterns as shown in FIG. 7. Two engaging grooves 41 are formed on two sides of a back face of the face board 4 corresponding to the lateral boards 32 of the housing 3 in width. In addition, several locating posts 411 are disposed in the engaging grooves 41 corresponding to the locating holes 321 of the housing 3, whereby the face board 4 can be engaged with the housing 3 with the lateral boards 32 inserted into the engaging grooves 41 and the locating posts 411 inserted into the locating holes 321. A joint section between the face board 4 and the housing 3 can be sealed by thermal fusion.

Figure 5:
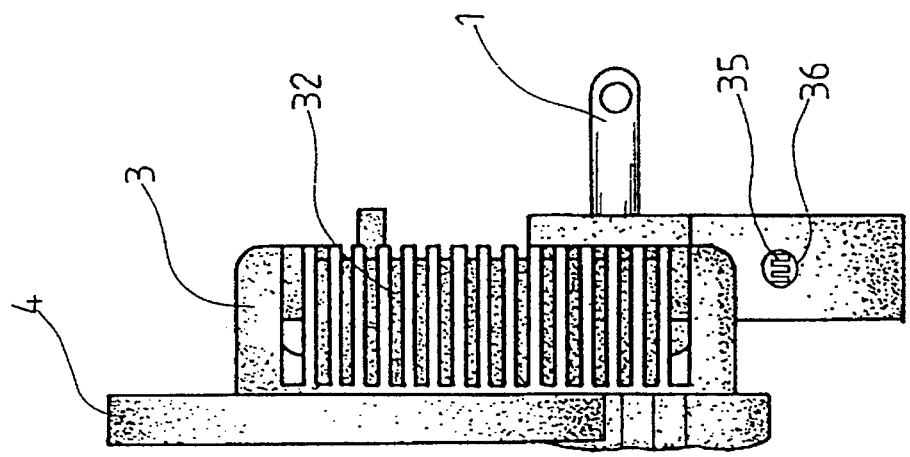
FIG. 5 is a side assembled view of the present invention.
Figure 6:
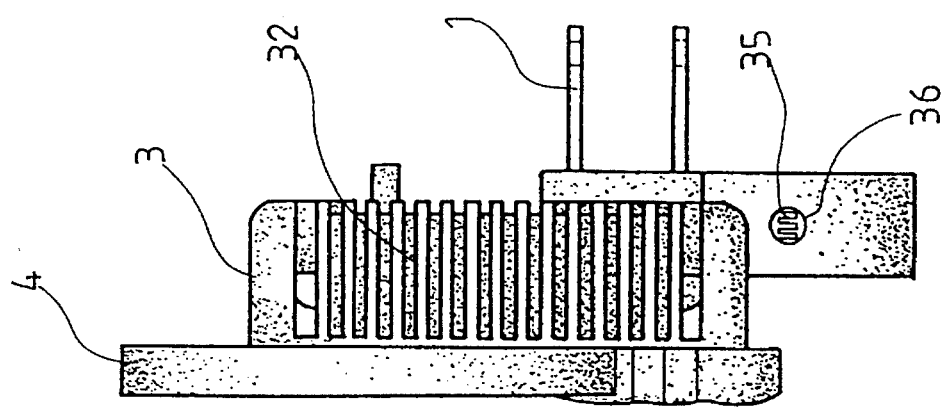
FIG. 6 is a side assembled view of the present invention in another pattern.

FIGS. 5 and 6 show two completed products of the present invention, wherein the copper plates 11 of the plug 1 in FIG. 5 are arranged in a vertically parallel pattern (US specification), while the copper plates 11 of the plug 1 in FIG. 6 are arranged in a horizontally parallel pattern (Taiwanese specification). When the perfumer is used by day, the optically sensitive element 35 will not work to turn on the lamp 341. However, when the perfumer is used at night or in a dim place, the optically sensitive element 35 activates the rectifier to turn on the lamp 341 which serves as a night lamp.

Referring to FIG. 7, when used, the solid perfume 5 is inserted into the insertion channel 31 of the housing 3 and the plug 1 is plugged into a power socket. At this time, the heat conductor 12 will generate heat and transmit the heat to the solid perfume 5 so as to vaporize the same into perfume gas.

The present invention has several advantages as follows:

1. The heat conductor is wrapped by the heat conductive and fireproof plastic material so that the safety in use is ensured. The night light is disposed under the perfumer and controlled by an optically sensitive element which turns on/off the light according to the ambient illumination. Therefore, the perfumer structure is powered on via a single power plug and has both the functions of dispersing perfume gas to clean the air and illuminating at night.

2. No matter whether the night light is turned on/off, the perfumer always disperses perfume gas to clean the air.

3. The copper plates of the plug have two patterns to meet different specifications of power sockets in US or Taiwan.

The above preferred embodiment are only examples of the present invention and the scope of the present invention should not be limited to the examples. Any modification or variation derived from the examples should fall within the scope of the present invention.

What is claimed is:

1. A perfumer structure with an optically controlled night lamp, comprising a heat conducting portion and a face board, said perfumer structure being characterized in that:

said heat conducting portion includes a plug formed by two identical bare copper plates, a heat conductor welded between said copper plates to form a circuit, a heat conductive and fireproof plastic material wrapping said copper plates and said heat conductor, and a plastic housing made by means of integral injection molding, said housing being formed with a central insertion channel for locating a solid perfume therein, two lateral boards being disposed on two sides of said insertion channel and several locating holes being formed on each lateral board, a convex guide rail being disposed at a central portion of said insertion channel for guiding the solid perfume when inserted into said insertion channel, said housing having a receptacle for receiving an optically controlled night lamp circuit board including a rectifier which converts AC into DC so as to supply power for a lamp, an optically sensitive element being disposed on one side of said receptacle for receiving ambient light and controlling said rectifier, a transparent cover being overlaid on said optically sensitive element for protecting an optically sensitive surface thereof; and said face board is associated with said housing, a front face of said face board can be designed with various patterns, two engaging grooves being formed on two sides of a back face of said face board corresponding to said lateral boards of said housing in width, several locating posts being disposed in said engaging grooves corresponding to said locating holes of said housing, whereby said face board can be engaged with said housing with said lateral boards inserted into said engaging grooves and said locating posts inserted into said locating holes, a joint section between said face board and said housing 3 being sealed by thermal fusion.

* * * * *